US010660517B2

(12) United States Patent
Yamada (10) Patent No.: US 10,660,517 B2
(45) Date of Patent: May 26, 2020

(54) AGE ESTIMATION USING FEATURE OF EYE MOVEMENT (71) Applicant: INTERNATIONAL BUSINESS MACHINES CORPORATION, Armonk, NY (US)

(72) Inventor: Yasunori Yamada, Saitama (JP)

(73) Assignee: International Business Machines Corporation, Armonk, NY (US)

(*) Notice: Subject to any disclaimer, the term of this patent is extended or adjusted under 35 U.S.C. 154(b) by 286 days.

(21) Appl. No.: 15/345,876

(22) Filed: Nov. 8, 2016

(65) Prior Publication Data

US 2018/0125356 A1 May 10, 2018

(51) Int. Cl.
A61B 3/00 (2006.01)
A61B 3/113 (2006.01)
A61B 3/11 (2006.01)
A61B 5/16 (2006.01)

(52) U.S. Cl.
CPC .............. *A61B 3/113* (2013.01); *A61B 3/112* (2013.01); *A61B 5/165* (2013.01)

(58) Field of Classification Search
CPC ......... A61B 3/113; A61B 3/112; A61B 5/165; A61B 5/7267; A61B 3/0091; A61B 5/163
See application file for complete search history.

(56) References Cited

U.S. PATENT DOCUMENTS

| | | | |
|---|---|---|---|
| 4,348,186 A | 9/1982 | Harvey et al. | |
| 4,513,317 A | 4/1985 | Ruoff, Jr. | |
| 4,634,384 A | 1/1987 | Neves et al. | |
| 5,204,703 A | 4/1993 | Hutchinson et al. | |
| 5,649,061 A | 7/1997 | Smyth | |
| 5,687,291 A | 11/1997 | Smyth | |
| 6,070,098 A | 5/2000 | Moore-Ede et al. | |
| 6,090,051 A | 7/2000 | Marshall | |
| 6,091,334 A | 7/2000 | Galiana et al. | |
| 6,102,870 A | 8/2000 | Edwards | |
| 6,346,887 B1 | 2/2002 | Van Orden et al. | |
| 7,344,251 B2 | 3/2008 | Marshall | |
| 7,431,455 B2 * | 10/2008 | Chernyak | A61B 3/11 351/205 |
| 7,438,418 B2 | 10/2008 | Marshall | |
| 7,791,491 B2 | 9/2010 | Johns | |

(Continued)

FOREIGN PATENT DOCUMENTS

| | | |
|---|---|---|
| JP | 2016079346 A | 4/2016 |
| WO | 2015/116832 A1 | 8/2015 |

OTHER PUBLICATIONS

Dowiasch, Stefan, et al. "Effects of Aging on Eye Movements in the Real World." Frontiers in Human Neuroscience, vol. 9, Oct. 2015, doi:10.3389/fnhum.2015.00046. (Year: 2015).*
Office Action issued in U.S. Appl. No. 15/345,845 dated Nov. 2, 2018, 19 pages.
Office Action issued in U.S. Appl. No. 15/346,034 dated Oct. 29, 2018, 14 pages.

(Continued)

*Primary Examiner* — Sean P Dougherty
*Assistant Examiner* — David Joseph Fernandez-Fidalgo
(74) *Attorney, Agent, or Firm* — Tutunjian & Bitetto, P.C.; Vazken Alexanian (57) ABSTRACT

A computer-implemented method for estimating an age of a target individual includes obtaining information of eye movement of the target individual, analyzing the information of the eye movement to extract a feature of the eye movement, and estimating the age of the target individual using the feature of the eye movement.

19 Claims, 6 Drawing Sheets

(56) References Cited

U.S. PATENT DOCUMENTS

| | | | |
|---|---|---|---|
| 8,678,589 B2 | 3/2014 | Sakata et al. | |
| 8,725,311 B1 | 5/2014 | Breed | |
| 2006/0126901 A1* | 6/2006 | Mattes | A61B 3/113 382/104 |
| 2006/0203197 A1* | 9/2006 | Marshall | A61B 3/112 351/246 |
| 2007/0066916 A1 | 3/2007 | Lemos | |
| 2007/0173733 A1 | 7/2007 | Le et al. | |
| 2007/0273611 A1 | 11/2007 | Torch | |
| 2007/0291232 A1 | 12/2007 | Marshall | |
| 2010/0085539 A1 | 4/2010 | Harada et al. | |
| 2011/0077548 A1 | 3/2011 | Torch | |
| 2011/0292342 A1 | 12/2011 | Maddess et al. | |
| 2015/0338915 A1 | 11/2015 | Publicover et al. | |
| 2016/0022136 A1 | 1/2016 | Ettenhoffer et al. | |
| 2017/0007119 A1 | 1/2017 | Cornsweet et al. | |
| 2017/0308909 A1* | 10/2017 | Faith | G06Q 30/0201 |
| 2018/0125357 A1 | 5/2018 | Suzuki et al. | |
| 2019/0025912 A1 | 1/2019 | Kimura et al. | |

OTHER PUBLICATIONS

List of IBM Patents or Patent Applications Treated as Related dated Nov. 8, 2016, 2 pages.

Abdulin et al., "User Fatigue Detection via Eye Movement Behavior", CHI EA 2015 Proceedings of the 33rd Annual ACM Conference Extended Abstracts on Human Factors in Computing Systems. Apr. 2015. pp. 1265-1270.

Guyon et al., "Gene Selection for Cancer Classification using Support Vector Machines", Machine Learning (Jan. 2002) vol. 46. pp. 389-422.

Yan et al., "Feature selection and analysis on correlated gas sensor data with recursive feature elimination", Sensors and Actuators B: Chemical. Jun. 2015. vol. 212. pp. 253-363.

Office Action issued in U.S. Appl. No. 15/346,034 dated Apr. 11, 2019, 24 pages.

Office Action issued in U.S. Appl. No. 15/345,845 dated Dec. 31, 2019, 25 pages.

Office Action issued in U.S. Appl. No. 15/346,034 dated Dec. 10, 2019, 20 pages.

* cited by examiner

AGE ESTIMATION USING FEATURE OF EYE MOVEMENT

BACKGROUND

Technical Field

The present invention, generally, relates to age estimation, and more particularly to techniques for estimating an age of an individual, and training a learning model that is used for estimating an age of an individual.

Related Art

Mental fatigue is of increasing importance to improve health outcomes and to support aging population. The costs of fatigue-related accidents and errors are estimated to be a considerable amount in society. Mental fatigue is also an important symptom in general practice due to its association with a large number of chronic medical conditions. Hence, there is a need for techniques for estimating a mental state such as mental fatigue to obviate a risk of accidents and errors and/or to early detection of disease. Accuracy of mental state estimation is also desired to be improved.

SUMMARY

According to an embodiment of the present invention, a computer-implemented method for estimating an age of a target individual is provided. The method includes obtaining information of eye movement of the target individual. The method also includes analyzing the information of the eye movement to extract a feature of the eye movement. The method further includes estimating the age of the target individual using the feature of the eye movement.

According to another embodiment of the present invention, a computer-implemented method for training a learning model that is used for estimating an age of a target individual is provided. The method includes preparing label information indicating an age of a participant and information of eye movement of the participant. The method also includes extracting a feature of the eye movement by analyzing the information of the eye movement. The method further includes training the learning model using one or more training data, each of which includes the label information and the features of the eye movement.

Computer systems and computer program products relating to one or more aspects of the present invention are also described and claimed herein.

Additional features and advantages are realized through the techniques of the present invention. Other embodiments and aspects of the invention are described in detail herein and are considered a part of the claimed invention.

BRIEF DESCRIPTION OF THE DRAWINGS

The subject matter, which is regarded as the invention, is particularly pointed out and distinctly claimed in the claims at the conclusion of the specification. The forgoing and other features and advantages of the invention are apparent from the following detailed description taken in conjunction with the accompanying drawings in which:

DETAILED DESCRIPTION

The present invention will be described using particular embodiments, and the embodiments described hereafter are understood to be only referred as examples and are not intended to limit the scope of the present invention.

One or more embodiments according to the present invention are directed to computer-implemented methods, computer systems and computer program products for estimating an age of a target individual using a feature of eye movement obtained from the target individual. One or more other embodiments according to the present invention are directed to computer-implemented methods, computer systems and computer program products for training a learning model using a feature of eye movement obtained from a participant, in which the learning model can be used for estimating an age of a target individual.

Hereinafter, referring to the series of FIGS. 1-5, a computer system and methods for training estimation models including an age estimation model and a mental fatigue estimation model, and estimating mental fatigue with an age of a target individual by using the estimation models according to an exemplary embodiment of the present invention will be described.

In an embodiment, the mental fatigue may be employed as a response variable for mental state estimation. However, in other embodiments, other mental state, such a mental workload, stress and sleepiness, may also be used as the response variable for the mental state estimation. In other embodiments, a mental state relating to mental health or some chronic medical condition, such as mental disorder, may also be used as the response variable for the mental state estimation in order to help medical diagnosis by professionals, such as doctors.

Figure 1:
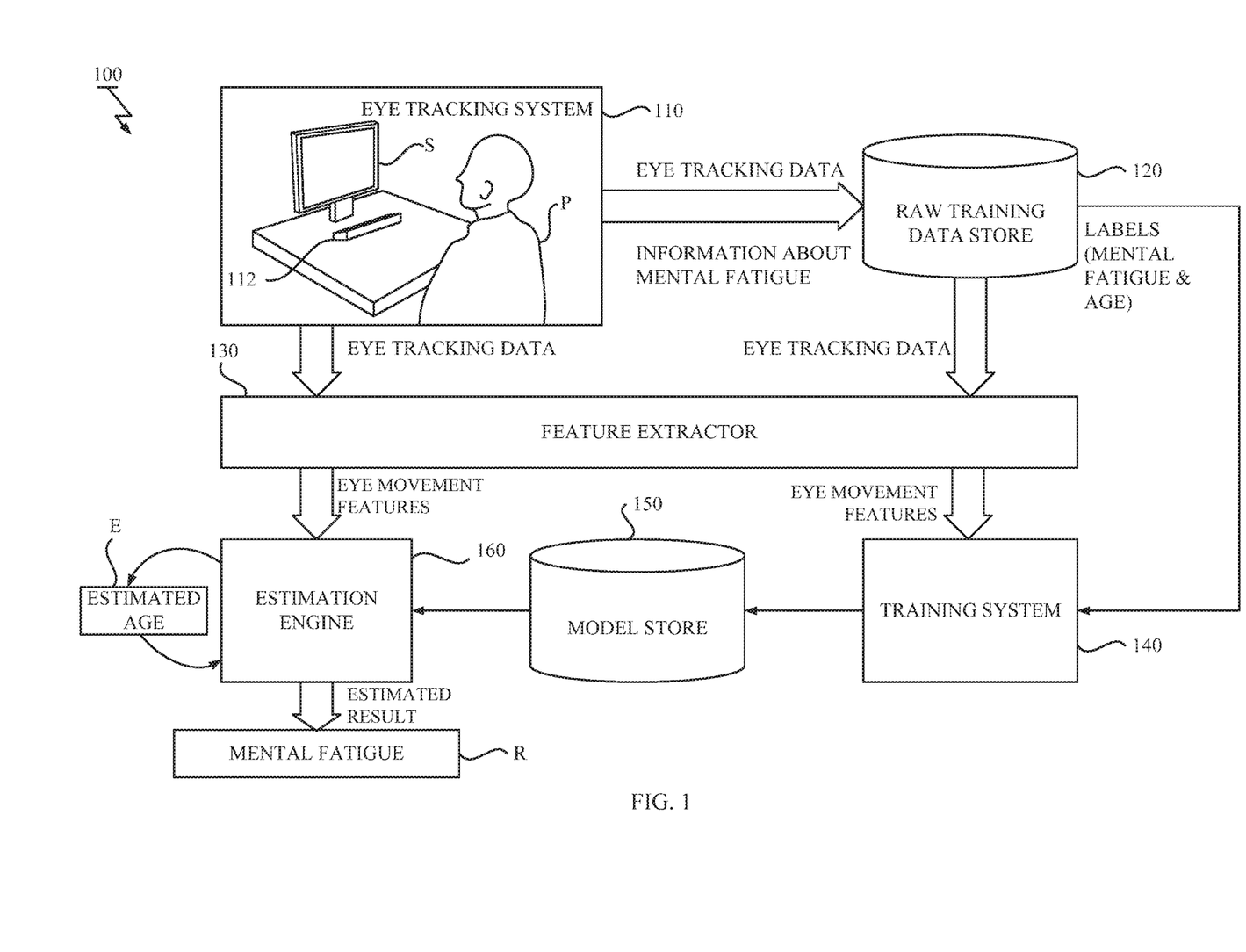
FIG. 1 illustrates a block/flow diagram of a mental fatigue estimation system according to an exemplary embodiment of the present invention.

FIG. 1 illustrates a block/flow diagram of a mental fatigue estimation system 100. As shown in FIG. 1, the mental fatigue estimation system 100 may include an eye tracking system 110, a raw training data store 120, a feature extractor 130, a training system 140, a model store 150, and an estimation engine 160.

The eye tracking system 110 may include an eye tracker 112 that is configured to acquire eye tracking data from a person P. The eye tracker 112 may be a device for measuring eye movement of the person P, which may be based on an optical tracking method using a camera or an optical sensor, electrooculogram (EOG) method, etc. The eye tracker 112 may be any one of non-wearable eye trackers or wearable eye trackers.

The person P may be referred to as a participant when the system 100 is in a training phase. The person P may be referred to as a target individual when the system 100 is in a test phase. The participant and the target individual may be same or may not be same, and may be any person in general.

The person P may watch a display screen S that shows a video and/or picture, while the eye tracker 112 acquires the eye tracking data from the person P. In an embodiment, the person P may be in natural-viewing conditions, where the person P watches freely a video and/or picture displayed on the display screen S while not performing any cognitive task. In an embodiment, unconstrained natural viewing of a video is employed as the natural-viewing situation.

However, in other embodiments, any kind of natural viewing conditions, which may include unconstrained viewing of scenery through a window opened in a wall, vehicle, etc., can also be employed. Furthermore, a condition where the eye tracking data is acquired may not be limited to the natural viewing conditions. In other embodiments, the eye tracker 112 may acquire the eye tracking data from the person P while the person P performs a task, such as driving.

The raw training data store 120 may store one or more raw training data, each of which includes a pair of eye tracking data acquired from the person P and label information. The label information includes a mental fatigue label indicating mental fatigue of the person P at a period during which the eye tracking data is acquired, and an age label indicating an age of the person P. The mental fatigue label may be given as subjective and/or objective measure, which may represent state of the mental fatigue (e.g., fatigue/non-fatigue) or degree of the mental fatigue (e.g. 0-10 rating scales). A (chronological) age (e.g., 35 years old) or a (chronological) age group (e.g., age group 30-39) of the person P can be used as the age label.

The feature extractor 130 may read the eye tracking data from the raw training data store 120 in the training phase. The feature extractor 130 may receive the eye tracking data from the eye tracker 112 in the test phase. The feature extractor 130 may be configured to extract one or more eye movement features from the eye tracking data for both age and mental fatigue estimations.

The feature extractor 130 may be configured to obtain information of eye movement of the person P and analyze the information of the eye movement to extract the one or more eye movement features. More detail about the eye movement features and extraction of the eye movement features will be described below.

In the training phase, the training system 140 may be configured to perform training of the age estimation model and the mental fatigue estimation model using one or more training data. Each training data used for training the age estimation model may include a pair of one or more eye movement features and the age label. Each training data used for training the mental fatigue estimation model may include a pair of one or more eye movement features and the mental fatigue label. The eye movement features for training may be extracted by the feature extractor 130 from the eye tracking data stored in the raw training data store 120. The age and mental fatigue label may be stored in the raw training data store 120 in association with the eye tracking data that is used to extract the corresponding eye movement features.

Figure 2A:
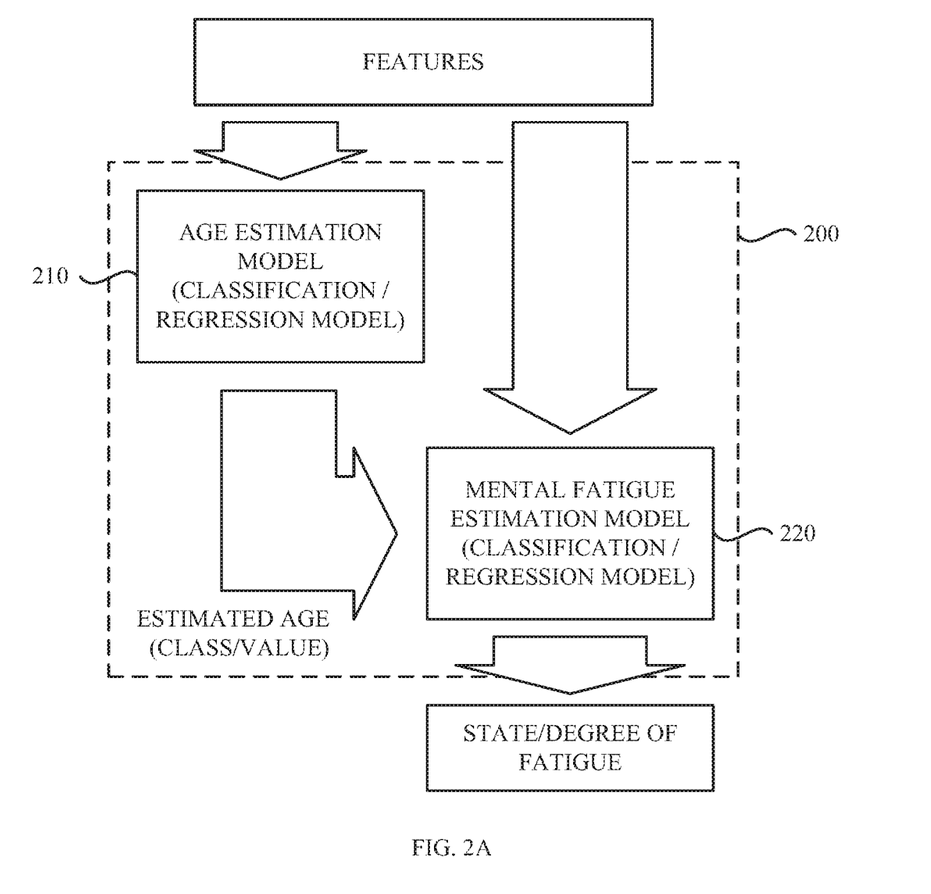
FIG. 2A depicts an example of an entire estimation model according to an embodiment of the present invention.

FIG. 2A depicts an example of an entire estimation model 200 according to an embodiment of the present invention. As shown in FIG. 2A, the entire estimation model 200 may include an age estimation model 210 and a mental fatigue estimation model 220.

The age estimation model 210 may be a learning model that receives one or more eye movement features as input and determines an estimated age of the person P (e.g., the target individual). The mental fatigue estimation model 220 may be a learning model that receives one or more eye movement features and the estimated age of the target individual P as input and determines a state or degree of the mental fatigue of the target individual P.

The age estimation model 210 may be a classification model that receives the one or more eye movement features as input and performs a classification task to determine an estimated age class of the person as discrete value (e.g., age group 30-39). Alternatively, the age estimation model 210 may be a regression model that receives the one or more eye movement features as input and performs a regression task to determine an estimated age value of the person P as continuous value (e.g., 42.5 years old).

Also, the mental fatigue estimation model 220 may be a classification model that receives the one or more eye movement features and the estimated age as input and performs a classification task to determine a state of the mental fatigue as discrete value (e.g., fatigue/non-fatigue). Alternatively, the mental fatigue estimation model 220 may be a regression model that receives the one or more eye movement features and the estimated age as input and performs a regression task to determine a degree of the mental fatigue as continuous value (e.g., 0-10 rating scales).

Any known learning models, such as ensembles of decision trees, SVM (Support Vector Machines), neural networks, etc., and corresponding appropriate machine learning algorithms can be employed for the estimation models 210, 220.

Note that the eye movement features used for the age estimation model 210 may be identical to or different from the eye movement features for the mental fatigue estimation model 220.

Figure 2B:
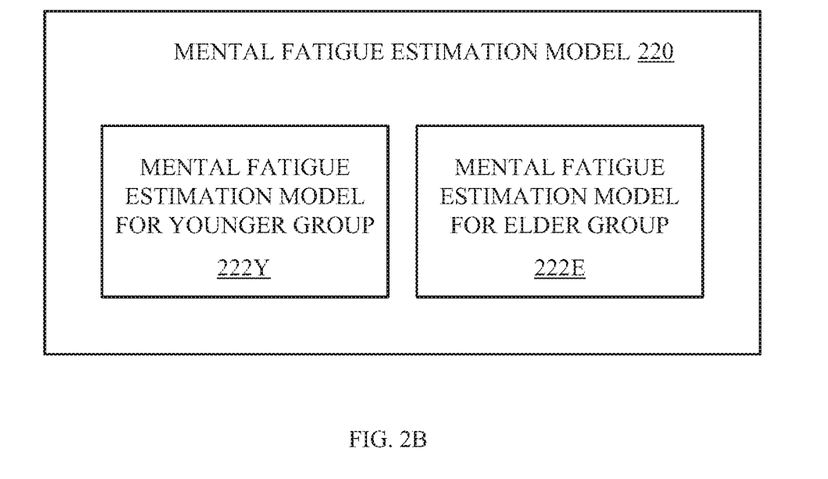
FIG. 2B depicts an example of a mental fatigue estimation model considering an age of a person according to an embodiment of the present invention.

FIG. 2B depicts an example of a mental fatigue estimation model 220 considering an age of the person P according to an embodiment of the present invention. As shown in FIG. 2B, the mental fatigue estimation model 220 may include a plurality of mental fatigue estimation models (e.g., 222Y and 222E), each of which is suitable for a respective age group (e.g., younger group/elder group).

If the estimated age is given as an age class, a mental fatigue estimation model corresponding to the age class estimated for the person P may be used to estimate the mental fatigue of the person P. If the estimated age is given as an age value, a mental fatigue estimation model (222Y/ 222E) corresponding to an age group to which the age value estimated for the person P belongs may be used to estimate the mental fatigue of the person P after performing appropriate thresholding.

By training each mental fatigue estimation model 222Y, 222E dedicated for the respective age group, the system 100 can estimate the mental fatigue in consideration of influence of age-related change in an oculomotor function of the target individual P to mental fatigue estimation. Note that the eye movement features used for one mental fatigue estimation model (e.g., 222Y) may be identical to or different from the eye movement features for the other mental fatigue estimation model (e.g., 222E).

However, the mental fatigue estimation model 220 may not be limited to the model shown in FIG. 2B. In another embodiment, the mental fatigue estimation model 220 may include a single mental fatigue estimation model that receives an age class or value as input in addition to the one or more eye movement features.

Referring back to FIG. 1, the model store 150 may be configured to store the age estimation model 210 and the mental fatigue estimation model 220 trained by the training system 140. After training these models 210, 220, the training system 140 may save parameters of the age estimation model 210 and the mental fatigue estimation model 220 into the model store 150.

In the test phase, the estimation engine 160 may be configured to estimate the mental fatigue of the target individual P using the age estimation model 210 and the mental fatigue estimation model 220 stored in the model store 150. The estimation engine 160 may receive the one or more features extracted from the eye tacking data of the target individual P, estimate an age of the target individual P as an intermediate result E and output the state or degree of the mental fatigue of the target individual P as an estimated result R.

In an embodiment, the age estimation model 210 may be the regression model and the mental fatigue estimation model 220 may have a plurality of the classification models 220L and 220H, each of which is used for respective age group. In this particular embodiment, the estimation engine 160 may determine the estimated age value of the target individual P by inputting the one or more eye movement features into the age estimation model 210. After performing thresholding the age value, the estimation engine 160 may determine the state of the mental fatigue by inputting the one or more eye movement features into the mental fatigue estimation model (222Y/222E) corresponding to an age group to which the estimated age value belongs.

In an embodiment, the estimation engine 160 can perform age and mental fatigue estimations without knowledge relating to content of the video and/or picture displayed on the display screen S.

In some embodiments, each of modules 120, 130, 140, 150 and 160 described in FIG. 1 may be implemented as, but not limited to, a software module including program instructions and/or data structures in conjunction with hardware components such as a processor, a memory, etc.; a hardware module including electronic circuitry; or a combination thereof. These modules 120, 130, 140, 150 and 160 described in FIG. 1 may be implemented on a single computer system, such as a personal computer, a server machine and a smartphone, or over a plurality of devices, such as a computer cluster of the computer systems in a distributed manner.

The eye tracking system 110 may be located locally or remotely to a computer system that implements the modules 120, 130, 140, 150 and 160 described in FIG. 1. The eye tracker 112 may be connected to the computer system via a computer-peripheral interface such as USB (Universal Serial Bus), Bluetooth™, etc. or through a wireless or wired network. Alternatively, the eye tracker 112 may be embedded into the computer system. In some embodiments, the eye tracking data may be provided to the computer system as a data file that is saved by a local or remote eye tracker, a data stream from a local eye tracker (connected to the computer system or embedded in the computer system), or a data stream via network socket from a remote eye tracker, which may be connected to or embedded in other remote computer systems, such as a laptop computer or smartphone. An existing camera included in the computer system may be utilized as a part of an eye tracker.

Hereinafter, referring to FIGS. 3A and 3B, the eye movement features used in the mental fatigue estimation system 100 will be described in more detail.

The eye tracking data acquired by the eye tracker 112 may include information of pupil, information of gaze and/or information of blink. The feature extractor 130 shown in FIG. 1 may be configured to extract one or more eye movement features from the information of the pupil, the information of the gaze and/or the information of the blink.

In an embodiment, the information of the pupil may include time series data representing pupil dynamics obtained from the target individual P and the one or more eye movement feature may include a pupil feature relating to the pupil dynamics. In further embodiments, the time series data may include first time series data obtained from one eye of the target individual P and second time series data obtained from other eye of the target individual P, and the pupil feature may be coordination relationship between the pupil dynamics of the both eyes of the target individual P.

Figure 3A:
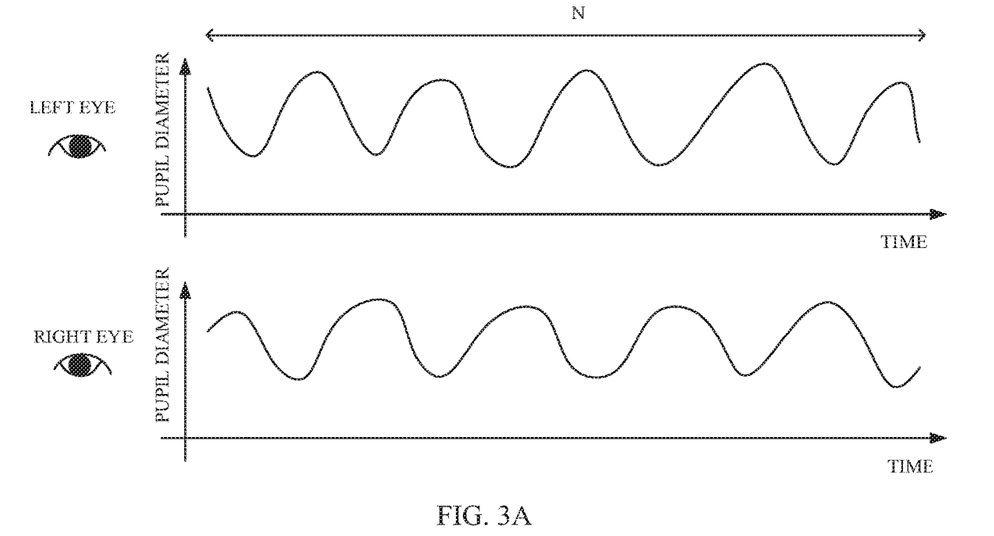
FIG. 3A illustrates schematic examples of time series data representing pupil dynamics obtained from both eyes of a person, which can be used to extract coordination relationship between pupil dynamics of both eyes according to an embodiment of the present invention.

FIG. 3A illustrates schematic examples of time series data representing pupil dynamics obtained from the both eyes of the person P, which can be used to extract the coordination relationship between pupil dynamics of both eyes.

The schematic examples of the time series data shown in FIG. 3A may be time series data of a pupil diameter of the left eye of the person P and time series data of a pupil diameter of the right eye of the person P. As schematically illustrated in FIG. 3A, each pupil diameter of individual eye fluctuates with time while indicating presence of some relation between both eyes. Hence, a coordination relationship between the fluctuation of the pupil diameter for the left eye and the fluctuation of the pupil diameter for the right eye can be defined.

In an embodiment, the coordination relationship may be calculated as a phase synchronization index between the time series data of the left eye and the time series data of the right eye. If phases of the two pupil dynamics are given, the phase synchronization index between the both eyes Φ can be calculated by the following equation:

$$\Phi = \left| \frac{1}{N} \sum_{t=1}^{N} e^{i[\phi_L(t) - \phi_R(t)]} \right|,$$

where $\phi_L(t)$ represents instantaneous phase of the pupil dynamics of the left eye, $\phi_R(t)$ represents instantaneous phase of the pupil dynamics of the right eye, N denotes data length and t is index of time. The instantaneous phase $\phi_X(t)$ can be calculated by the following equation:

$$\phi_X(t) = \tan^{-1} \frac{f_X^H(t)}{f_X(t)} \text{(for } X = L \text{ or } R\text{),}$$

where $f_X(t)$ represents the time series data of the pupil diameter of the left eye (X=L) or the right eye (X=R), and $f^H_X(t)$ represents the Hilbert transform of $f_X(t)$.

A series of phase synchronization indices obtained by sliding a time window, or mean, median and/or maximum value among the series of the obtained synchronization indices can be used as the one or more extended features. The width of the time window may also be varied. Instead of using the Hilbert transform, Wavelet transform may also be used to obtain the phase of the time series data.

In another embodiment, the coordination relationship may be calculated as a correlation value between the time series data of the left eye and the time series data of the right eye.

The correlation value between the time series data of the both eyes with time lag k can be calculated by the following equation:

$$\text{Correlation value}(k) = \frac{C_{LR}(k)}{\sqrt{C_{LL}(0)}\sqrt{C_{RR}(0)}},$$

$$\text{where } C_{XY}(k) = \frac{1}{N}\sum_{t=1}^{N} F_X(t)F_Y(t+k)(\text{for } XY = LR, LL, \text{ or } RR),$$

where $F_X(t)$ represents normalized data of the time series data of the pupil diameter $f_X(t)$ of the left eye (X=L) or the right eye (X=R).

A series of correlation values (with zero time lag or with one or more time lags) obtained by sliding a time window, or mean, median and/or maximum value among the series of the obtained correlation values can be used as the one or more extended features. The width of the time window may also be varied.

The feature extractor 130 may analyze the time series data of the pupil diameter of the left eye and the time series data of the pupil diameter of the right eye to extract the phase synchronization index and/or correlation value.

However, the eye movement features may not be limited to the aforementioned coordination relationship. In another embodiment, other features derived from at least one selected from a group including saccade amplitude, saccade duration, saccade rate, inter-saccade interval, mean velocity of saccade, peak velocity of saccade, blink duration, blink rate, inter-blink interval, an average diameter of a pupil of an individual eye, constriction velocity of the pupil of the individual eye, amplitude of the pupil of the individual eye, a frequency distribution of fixation in polar coordinate system and a direction of eye movement may be used as the eye movement feature in place of or in addition to the aforementioned coordination relationship between pupil dynamics of both eyes.

Hereinafter, referring to FIG. 3B, a frequency distribution of the fixation, which can be used as one of the eye movement features, will be described in more detail. The time series data of the point of the gaze may include a component of fixation and a component of saccade. The fixation is the maintaining of the gaze on a location. The saccade is movement of the eyes between two or more phases of the fixation. The components of the fixation and the component of the saccade can be identified and separated by using any known algorithm, including algorithms using velocity and/or acceleration thresholds, dispersion-based algorithms, area-based algorithms, etc.

Figure 3B:
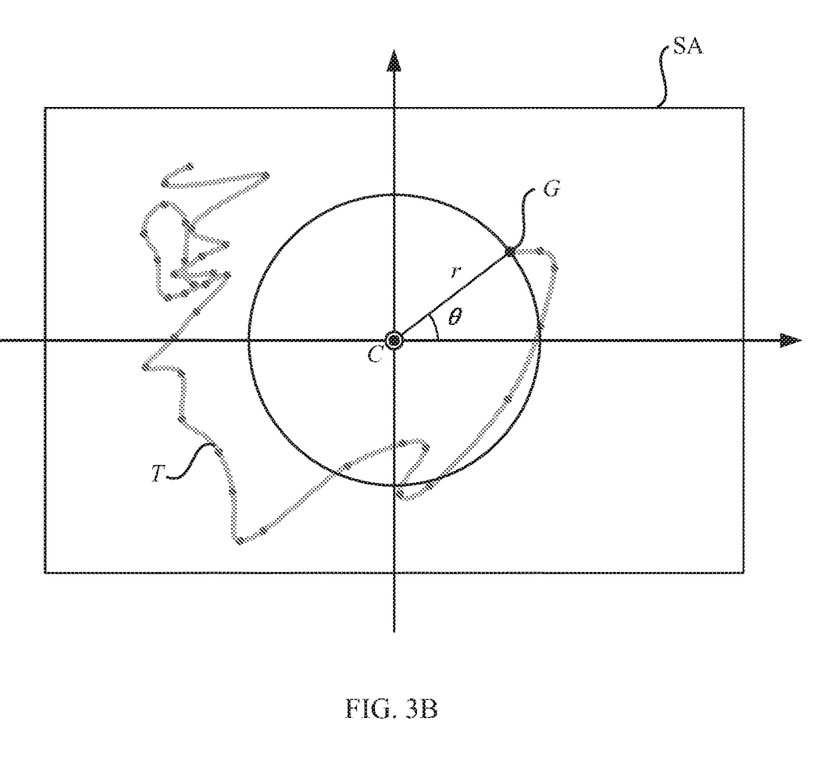
FIG. 3B illustrates an example of a coordinate system used for extracting frequency distribution of fixation according to an embodiment of the present invention.

FIG. 3B illustrates an example of a coordinate system used for extracting frequency distribution of fixation. Typically, the point of the gaze acquired by the eye tracker 112 may be defined in a Cartesian coordinate system on the display screen S. To extract the extended features, the feature extractor 130 first obtain the time series data of the point of the gaze in a polar coordinate system by performing coordinate transformation from the original coordinate system to the polar coordinate system.

The polar coordinate system may determine the point of the gaze G by an angle θ and a distance r with respect to a reference point C. The reference point C may be related to a center of an area SA corresponding to the display screen S showing a video and/or picture as the scene, and the reference point C may be placed at the center of the display screen S. In an embodiment, calibration of the reference point C can be done by directing the person P to look at a specific point, such as the center of the display screen S for example.

In the polar coordinate system shown in FIG. 3B, the time series data of the point of the gaze T with a certain time length may draw a trajectory. The feature extractor 130 may analyze the time series data of the point of the gaze T defined in the polar coordinate system to extract a frequency distribution of fixation (r, θ). The frequency distribution of the fixation (r, θ) may include a plurality of cells or meshes, each of which holds a (relative) frequency of the fixation detected at a region designated by the row and the column from the time series data of the point of the gaze T.

However, in other embodiments, the frequency distribution of the fixation (r) and the frequency distribution of the fixation (θ) calculated independently from the time series data of the point of the gaze T may be used as the eye movement features in place of or in addition to the frequency distribution of the fixation (r, θ) in 2D form. Also entropy and/or static (e.g., mean, median, standard deviation, etc.) of the fixation (r, θ) may also be used as the eye movement features in addition to the frequency distribution.

The aforementioned eye movement features including the coordination relationship and the frequency distribution of the fixation may be used as a part of or whole of explanatory variables of the age estimation model 210 and the mental fatigue estimation model 220.

Hereinafter, referring to FIG. 4, a novel process for learning the estimation models 210, 220 will be described.

Figure 4:
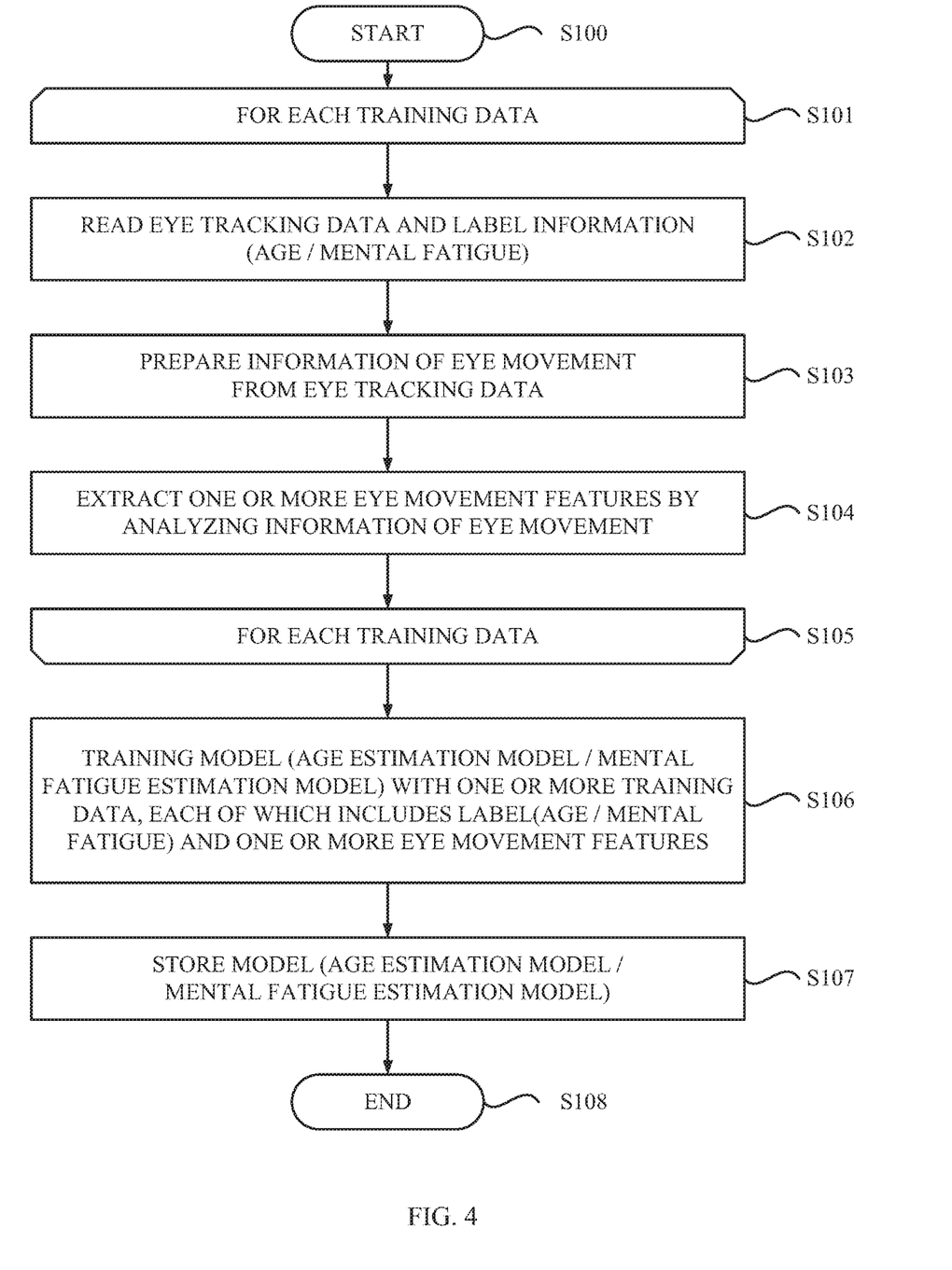
FIG. 4 is a flowchart depicting a process for learning an age or mental fatigue estimation model according to an embodiment of the present invention.

FIG. 4 shows a flowchart depicting a process for learning the age estimation model 210 or the mental fatigue estimation model 220 in the mental fatigue estimation system 100 shown in FIG. 1. Note that the process shown in FIG. 4 may be performed by a processing unit that implements the feature extractor 130 and the training system 140 shown in FIG. 1. Also note that FIG. 4 shows the process for learning the age estimation model 210 and the process for training the mental fatigue estimation model 220 comprehensively.

The process shown in FIG. 4 may begin at step S100 in response to receiving a request for training with one or more arguments. One of the arguments may specify a group of the raw training data to be used for training. The processing from step S101 to S105 may be performed for each training data to be prepared.

At step S102, the processing unit may read the eye tracking data and corresponding label information from the raw training data store 120 and set the label information into the training data. If the process shown in FIG. 4 is performed for training the age estimation model 210, the age label indicating an age of the participant P may be read and set into the training data. If the process shown in FIG. 4 is performed for training the mental fatigue estimation model 220, the mental fatigue label indicating mental fatigue of the person P may be read and set into the training data.

At step S103, the processing unit may prepare the information of the eye movement from the eye tracking data. The information of the eye movement may include the information of the pupil, the information of the gaze and/or the information of the blink.

At step S104, the processing unit may extract the eye movement features by analyzing the information of the eye movement. In an embodiment, the processing unit may analyze time series data of the pupil diameter of the left eye and the time series data of the pupil diameter of the right eye to calculate the phase synchronization indices and/or correlation values in the step S104. The processing unit may set the extracted eye movement features into the training data as the features. Also note that if the process is performed for training the mental fatigue estimation model 220, the processing unit may set the age label into the training data as an additional feature.

During the loop from the step S101 to the step S105, the processing unit may prepare one or more training data by using the given raw training data. If the processing unit determines that a desired amount of the training data has been prepared or analysis of all given raw training data has been finished, the process may exit the loop and the process may proceed to step S106.

At step S106, the processing unit may perform training of the age estimation model 210 or the mental fatigue estimation model 220 by using an appropriate machine laming algorithm with the prepared training data. Each training data for the age estimation model 210 may include the age label obtained at step S102 and the eye movement features obtained at the step S104. Each training data for the mental fatigue estimation model 220 may include the mental fatigue label obtained at step S102, the eye movement features obtained at the step S104 and the age label obtained at step S102 as the additional feature.

In an embodiment using the plurality of the mental fatigue estimation models, each of which is dedicated for the respective age group, the training data may be divided into a plurality of groups on the basis of the age label, and each mental fatigue estimation model dedicated for the respective age group may be trained by using the training data in the respective group.

At step S107, the processing unit may store the trained parameter of the age estimation model 210 or the mental fatigue estimation model 220 into the model store 150 and the process may end at step S108. The training of the age estimation model 210 and the training of the mental fatigue estimation model 220 may be conducted separately or all at once.

Hereinafter, referring to FIG. 5, a novel process for estimating mental fatigue with an age of the person P using the age and mental fatigue estimation models 210, 220 trained by the process shown in FIG. 4 will be described.

Figure 5:
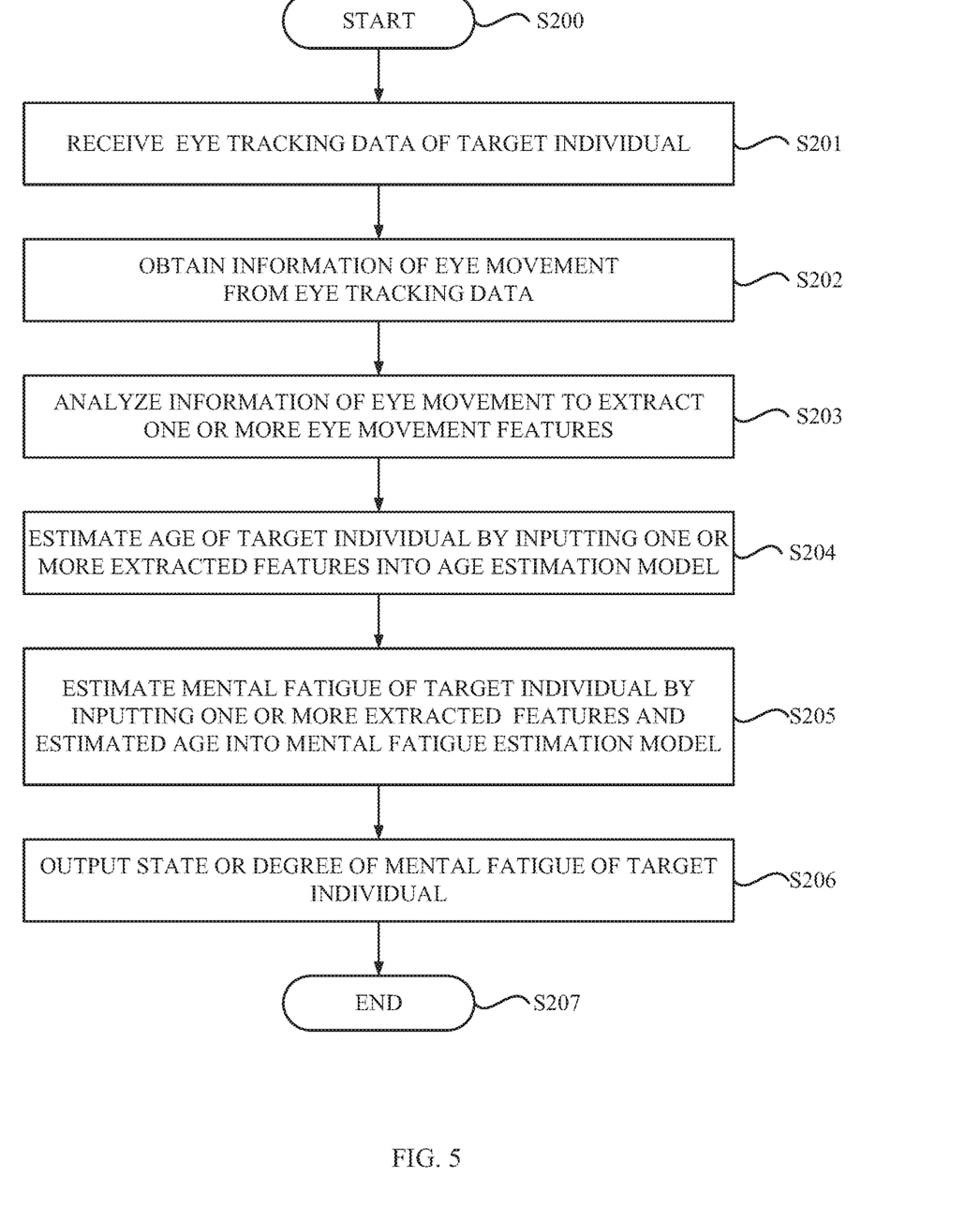
FIG. 5 is a flowchart depicting a process for estimating mental fatigue with an age of a person using the trained age and mental fatigue estimation models according to an embodiment of the present invention.

FIG. 5 is a flowchart depicting a process for estimating mental fatigue with an age of a target individual P using the trained age and mental fatigue estimation in the mental fatigue estimation system 100 shown in FIG. 1. Note that the process shown in FIG. 5 may be performed by a processing unit that implements the feature extractor 130 and the estimation engine 160 shown in FIG. 1. Also note that the eye movement features used in the process shown in FIG. 5 may be identical to those used in the process shown in FIG. 4.

The process shown in FIG. 5 may begin at step S200 in response to receiving a request for estimating mental fatigue of a target individual P. At step S201, the processing unit may receive eye tracking data acquired by the eye tracker 112 from the target individual P.

At step S202, the processing unit may obtain the information of the eye movement from the eye tracking data. At step 203, the processing unit may analyze the information of the eye movement to extract the one or more eye movement features. In an embodiment, the processing unit may analyze time series data of the pupil diameter of the left eye and the time series data of the pupil diameter of the right eye to calculate the phase synchronization indices and/or the correlation values in the step S203.

At step S204, the processing unit may estimate an age of the target individual P by inputting one or more extracted features into the age estimation model 210. At step S205, the processing unit may estimate mental fatigue of the target individual P by inputting one or more eye movement features, which may be same as or difference from the one or more extracted feature used at step S204, and the estimated age of the target individual P into the mental fatigue estimation model 220.

In an embodiment using the plurality of the mental fatigue estimation models, the processing unit may estimate the mental fatigue of the target individual P by inputting the movement features into a mental fatigue estimation model 222 corresponding to the estimated age. At step S206, the processing unit may output the state or degree of the mental fatigue of the target individual P and the process may end at step S207.

Experimental Studies

A program implementing the system shown in FIG. 1 and the process shown in FIGS. 4 and 5 according to the exemplary embodiment was coded and executed for given training samples and test samples.

The samples were obtained from a total of 15 participants (7 females, 8 males; 24-76 years; mean (SD) age 51.7 (19.9) years). The eye tracking data was acquired from each participant while the participant was watching a video clip of 5 minutes before and after doing a mental calculation task of approximately 35 minutes by hearing questions, which required no visual processing. Each 5-min phase for video watching consisted of nine short video clips of 30 seconds. The eye tracking data of each 30 seconds obtained between breaks was used as one sample. The states of the mental fatigue of the participants were confirmed by observing statistically significant increment in both of subjective measure (0-10 rating scales) and objective measure (pupil diameter). The eye tracking data collected before the mental calculation task was labelled as "non-fatigue" and the eye tracking data collected after the task was labelled as "fatigue". Thus, the numbers of the samples for both "non-fatigue" and "fatigue" states were 9*15=135, respectively. Chronological ages of the participants were used as the age label.

Features related to oculomotor measures (fixation and saccade components), blink behavior and pupil diameter were employed as a first set of eye movement features (I). Features related to oculomotor measures (fixation and saccade components), blink behavior, pupil diameter and coordination relationship between pupil dynamics of both eyes were employed as a second set of eye movement features (II). The feature related to the oculomotor measures included the frequency distribution of the fixation with 36 ranges of the angle $\theta$ and 8 ranges of the distance r, features derived from the direction of the eye movement and the saccade component. Mean values of the phase synchronization indices and the correlation values with different time windows (e.g., 5, 15, 30, 60 frames, sampling rate=60 Hz) were employed as the coordination relationship.

A regression model of v-support vector regression (SVR) with a radial basis kernel function and an improved SVM-recursive feature elimination algorithm with a correlation bias reduction strategy in the feature elimination procedure were used as the age estimation model.

As examples, the regression model was trained by using either the first set of the eye movement feature (I) or the second set of the eye movement features (II) in the prepared training samples.

Age estimation accuracy using the regression model was evaluated by root means square error (RMSE), which was calculated from test samples according to 10-fold cross-validation method. The evaluated results of the example for the age estimation are summarized as follows:

| Root means Square Error (RMSE) | |
|---|---|
| Example 1 (first set (I): w/o coordination relationship) | Example 2 (second set (II): w/coordination relationship) |
| 7.9 years in age | 7.4 years in age |

A classification model of 2-class support vector machine (SVM) with a radial basis function kernel and improved SVM-recursive feature elimination algorithm with a correlation bias reduction strategy in the feature elimination procedure were used as the mental fatigue estimation model.

As a comparative example, one 2-class classification model was trained by using the second set of the eye movement features (II) in the prepared training samples. As an example, two 2-class classification models were trained independently by using the second set of the eye movement features (II) in respective training samples. The training samples were divided into two groups using a predetermined age threshold. Unless otherwise noted, any portions of the classification model were approximately identical between the example and the comparative example.

Classification performance of the mental fatigue estimation using the classification model was evaluated by 2-class classification accuracy, which was calculated from test samples according to 10-fold cross-validation method. The evaluated results of the example and the comparative example for mental fatigue estimation are summarized as follows:

| Classification accuracy (chance rate 50%) | | |
|---|---|---|
| Comparative Example (one 2-class classification model) | Example 3 (two 2-class classification model) | improvement |
| 86% | 97% | approximately 11% |

By comparison with the result of the comparative example, the accuracy of the Example 3 increased by approximately 11%.

Computer Hardware Component

Figure 6:
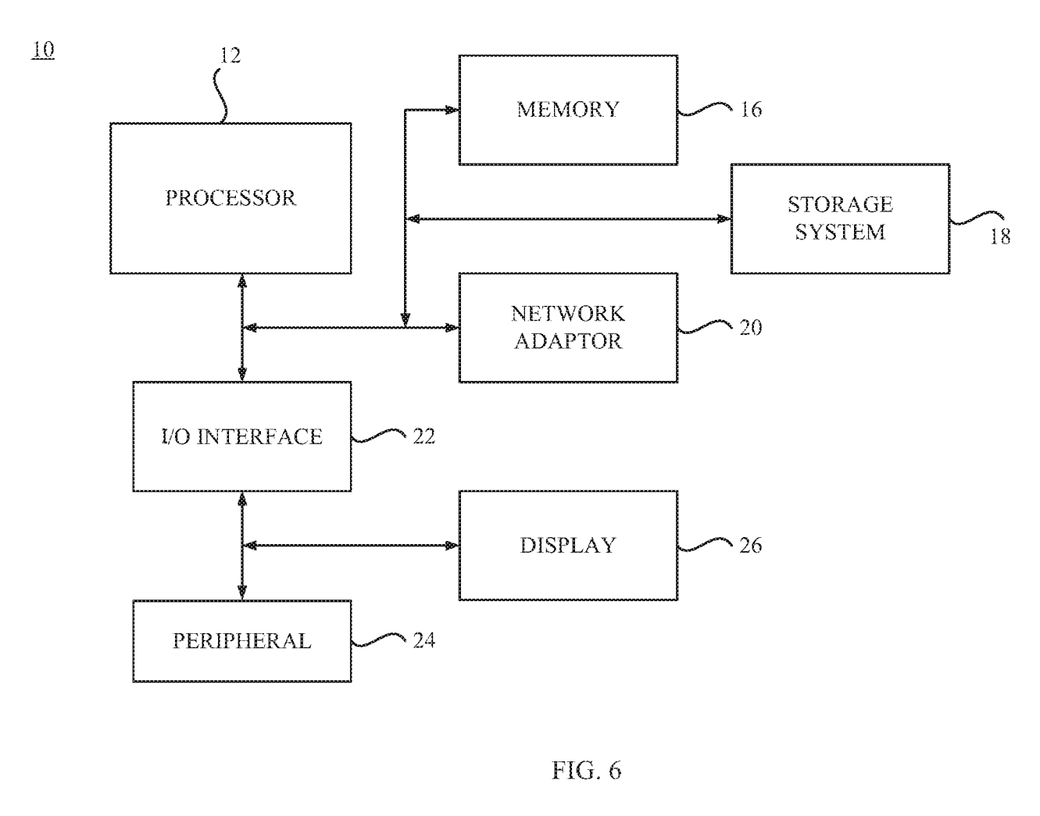
FIG. 6 depicts a computer system according to an embodiment of the present invention.

Referring now to FIG. 6, a schematic of an example of a computer system 10, which can be used for the mental fatigue estimation system 100, is shown. The computer system 10 shown in FIG. 6 is implemented as a computer system. The computer system 10 is only one example of a suitable processing device and is not intended to suggest any limitation as to the scope of use or functionality of embodiments of the invention described herein. Regardless, the computer system 10 is capable of being implemented and/or performing any of the functionality set forth hereinabove.

The computer system 10 is operational with numerous other general purpose or special purpose computing system environments or configurations. Examples of well-known computing systems, environments, and/or configurations that may be suitable for use with the computer system 10 include, but are not limited to, personal computer systems, server computer systems, thin clients, thick clients, hand-held or laptop devices, in-vehicle devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system 10 may be described in the general context of computer system-executable instructions, such as program modules, being executed by a computer system. Generally, program modules may include routines, programs, objects, components, logic, data structures, and so on that perform particular tasks or implement particular abstract data types.

As shown in FIG. 6, the computer system 10 is shown in the form of a general-purpose computing device. The components of the computer system 10 may include, but are not limited to, a processor (or processing unit) 12 and a memory 16 coupled to the processor 12 by a bus including a memory bus or memory controller, and a processor or local bus using any of a variety of bus architectures.

The computer system 10 typically includes a variety of computer system readable media. Such media may be any available media that is accessible by the computer system 10, and it includes both volatile and non-volatile media, removable and non-removable media.

The memory 16 can include computer system readable media in the form of volatile memory, such as random access memory (RAM). The computer system 10 may further include other removable/non-removable, volatile/non-volatile computer system storage media. By way of example only, the storage system 18 can be provided for reading from and writing to a non-removable, non-volatile magnetic media. As will be further depicted and described below, the storage system 18 may include at least one program product having a set (e.g., at least one) of program modules that are configured to carry out the functions of embodiments of the invention.

Program/utility, having a set (at least one) of program modules, may be stored in the storage system 18 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments of the invention as described herein.

The computer system 10 may also communicate with one or more peripherals 24, such as a keyboard, a pointing device, a car navigation system, an audio system, etc.; a display 26; one or more devices that enable a user to interact with the computer system 10; and/or any devices (e.g., network card, modem, etc.) that enable the computer system 10 to communicate with one or more other computing devices. Such communication can occur via Input/Output (I/O) interfaces 22. Still yet, the computer system 10 can communicate with one or more networks such as a local area network (LAN), a general wide area network (WAN), and/or a public network (e.g., the Internet) via the network adapter 20. As depicted, the network adapter 20 communicates with the other components of the computer system 10 via bus. It should be understood that although not shown, other hardware and/or software components could be used in conjunction with the computer system 10. Examples, include, but are not limited to: microcode, device drivers, redundant processing units, external disk drive arrays, RAID systems, tape drives, and data archival storage systems, etc.

Computer Program Implementation

The present invention may be a computer system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more aspects of the present invention has been presented for purposes of illustration and description, but is not intended to be exhaustive or limited to the invention in the form disclosed.

Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for estimating an age of a target individual, the method comprising:
    obtaining information of eye movement of the target individual;
    analyzing the information of the eye movement to extract one or more features of the eye movement;
    outputting, via an age estimation model performing a classification task, an estimated age value of the target individual using the one or more features of the eye movement; and
    estimating, via a mental fatigue estimation model performing a classification task, a mental state of the target individual using one or more eye movement features obtained from the target individual and the age estimated for the target individual for detection of disease and/or chronic medical condition.

2. The method of claim 1, wherein the information of the eye movement includes time series data representing pupil dynamics obtained from the target individual and the feature of the eye movement includes a pupil feature relating to the pupil dynamics.

3. The method of claim 2, wherein the time series data includes first time series data obtained from a first eye of the target individual and second time series data obtained from a second eye of the target individual, and the pupil feature is a coordination relationship between the pupil dynamics of both the first eye and the second eye of the target individual.

4. The method of claim 3, wherein the coordination relationship is calculated as a phase synchronization index and/or a correlation value between the first and second time series data.

5. The method of claim 3, wherein the first time series data and the second time series data are time series data of a pupil diameter of the first eye of the target individual and time series data of a pupil diameter of the second eye of the target individual, respectively.

6. The method of claim 3, wherein the feature of the eye movement includes one or more features selected from a group including saccade amplitude, saccade duration, saccade rate, inter-saccade interval, mean velocity of saccade, peak velocity of saccade, blink duration, blink rate, inter-blink interval, an average diameter of a pupil of an individual eye, constriction velocity of the pupil of the individual eye, amplitude of the pupil of the individual eye, a frequency distribution of fixation in a polar coordinate system and a direction of the eye movement, in addition to the coordination relationship.

7. The method of claim 1, wherein estimating of the age comprises determining a class indicating the age of the target individual by using a first learning model, the first learning model receiving the feature of the eye movement as input.

8. The method of claim 7, wherein the first learning model is trained using one or more training data for age estimation, each training data including label information indicating an age of a participant and a feature of eye movement extracted from information of the eye movement of the participant.

9. The method of claim 1, wherein the one or more eye movement features include one or more features selected from a group including saccade amplitude, saccade duration, saccade rate, inter-saccade interval, mean velocity of saccade, peak velocity of saccade, blink duration, blink rate, inter-blink interval, an average diameter of a pupil of an individual eye, constriction velocity of the pupil of the individual eye, amplitude of the pupil of the individual eye, a frequency distribution of fixation in a polar coordinate system, a direction of the eye movement, and a coordination relationship between pupil dynamics of both a first eye and a second eye of the target individual.

10. The method of claim 1, wherein estimating of the mental state comprises determining a state or a degree non-transitory of mental fatigue as the mental state by using a second learning model, the second learning model receiving the one or more eye movement features and the age of the target individual as input and performing classification or regression.

11. The method of claim 10, wherein the second learning model includes a plurality of models, each model representative of a respective group of the age.

12. The method of claim 10, wherein the second learning model is trained using one or more training data for mental fatigue estimation, each training data including label information indicating mental fatigue of a participant, one or more eye movement features of the participant and an age of the participant.

13. A computer-implemented method for training a learning model used for estimating an age of a target individual, the method comprising:
    preparing label information indicating an age, a mental state, and information of eye movement of the participant;
    extracting one or more features of the eye movement by analyzing the information of the eye movement;
    training the learning model using one or more training data, each training data including the label information and the one or more features of the eye movement;
    outputting, via an age estimation model performing a classification task, an estimated age value of the target individual using the one or more features of the eye movement; and
    estimating, via a mental fatigue estimation model performing a classification task, a mental state of the target individual using one or more eye movement features obtained from the target individual and the age estimated for the target individual for detection of disease and/or chronic medical condition.

14. The method of claim 13, wherein the information of the eye movement includes time series data representing pupil dynamics obtained from the participant and the feature of the eye movement includes a pupil feature relating to the pupil dynamics.

15. A computer system for estimating an age of a target individual, by executing program instructions, the computer system comprising:

a memory tangibly storing the program instructions; and
a processor in communications with the memory,
wherein the processor is configured to:
   obtain information of eye movement of the target individual;
   analyze the information of the eye movement to extract one or more features of the eye movement;
   output, via an age estimation model performing a classification task, an estimated age value of the target individual using the one or more features of the eye movement; and
   estimate, via a mental fatigue estimation model performing a classification task, a mental state of the target individual using one or more eye movement features obtained from the target individual and the age estimated for the target individual for detection of disease and/or chronic medical condition.

16. The computer system of claim 15, wherein the information of the eye movement includes time series data representing pupil dynamics obtained from a participant and the feature of the eye movement includes a pupil feature relating to the pupil dynamics.

17. The computer system 16, wherein the time series data includes first time series data obtained from a first eye of the target individual and second time series data obtained from a second eye of the target individual, and the pupil feature is a coordination relationship between the pupil dynamics of both the first eye and the second eye of the target individual.

18. The computer system of claim 16, wherein the processor is further configured to determine a class indicating the age of the target individual by using a first learning model, the first learning model receiving the feature of the eye movement as input and performing classification.

19. A computer program product for estimating an age of a target individual, the computer program product comprising a non-transitory computer readable storage medium having program instructions embodied therewith, the program instructions executable by a computer to cause the computer to perform the method of claim 1.

* * * * *